(12) United States Patent
Hölzl et al.

(10) Patent No.: US 7,208,597 B2
(45) Date of Patent: Apr. 24, 2007

(54) PYRIDYL-TRIAZINE DERIVATIVES AS MICROBIOCIDAL ACTIVE SUBSTANCES

(75) Inventors: Werner Hölzl, Eschentzwiller (FR); Gabriele Eichacker, Eimeldingen (DE); Andrea Preuss, Basel (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/522,925

(22) PCT Filed: Jul. 22, 2003

(86) PCT No.: PCT/EP03/07975

§ 371 (c)(1),
(2), (4) Date: Jan. 25, 2005

(87) PCT Pub. No.: WO2004/013124

PCT Pub. Date: Feb. 12, 2004

(65) Prior Publication Data

US 2005/0267109 A1 Dec. 1, 2005

(30) Foreign Application Priority Data

Jul. 31, 2002 (EP) ................... 02405669

(51) Int. Cl.
*C07D 401/04* (2006.01)
*A01N 43/66* (2006.01)
(52) U.S. Cl. ................... 544/212; 514/245; 252/301.23
(58) Field of Classification Search ................ 544/216, 544/212; 514/241, 245; 252/301.23
See application file for complete search history.

(56) References Cited

U.S. PATENT DOCUMENTS 5,250,530 A 10/1993 Giencke et al. ............. 514/256

FOREIGN PATENT DOCUMENTS

| DE | 197 35 800 A1 * | 2/1999 |
|---|---|---|
| EP | 0407899 | 1/1991 |
| EP | 0515942 | 12/1992 |
| WO | 98/57957 | 12/1998 |
| WO | 02/053560 | 7/2002 |

OTHER PUBLICATIONS

Snyder et al., J. Med. Liban 48(4): 208-214, 2000.*
Kelarev et al., Khimiya Geterotsiklicheskikh Soedinenii 5, 674-680, 1988, CA 110: 114800, 1989.*

* cited by examiner

*Primary Examiner*—Venkataraman Balasubramanian
(74) *Attorney, Agent, or Firm*—Joseph C. Suhadolnik; Kevin T. Mansfield

(57) ABSTRACT

Triazine derivatives of formula (1) wherein $R_1$ is $C_1$–$C_{20}$alkyl; $C_3$–$C_7$cycloalkyl; or $C_1$–$C_{20}$perfluoroalkyl; $R_2$ is hydrogen; $C_1$–$C_{20}$alkyl; or $C_3$–$C_7$cycloalkyl; and $R_3$ is hydrogen; $C_1$–$C_{20}$alkyl; $C_3$–$C_7$cycloalky; $C_1$–$C_{20}$perfluoroalky; $C_1C_{20}$alkyl-carbonyl; $C_3$–$C_7$cycloalkyl-carbonyl; $C_1$–$C_{20}$perfluoroalkyl-carbonyl; or phenylcarbonyl; are described. The compounds exhibit pronounced action against gram-positive and gram-negative bacteria and also against yeasts and moulds. They are also suitable for treating or preventing biofilms on human tooth surfaces and oral mucosa

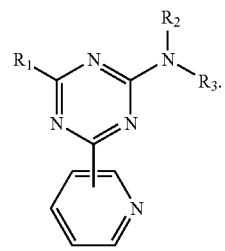

(1)

4 Claims, 1 Drawing Sheet

PYRIDYL-TRIAZINE DERIVATIVES AS MICROBIOCIDAL ACTIVE SUBSTANCES

The present invention relates to selected 2-alkyl-4-amino-6-pyridyl-1,3,5-triazine derivatives, to the preparation of such compounds, and to the use of such compounds in the antimicrobial treatment of surfaces, as antimicrobial active substances against gram-positive and gram-negative bacteria, yeasts and fungi and also in the preservation of cosmetics, household products, textiles and plastics and for use in disinfectants.

The compounds according to the invention correspond to formula

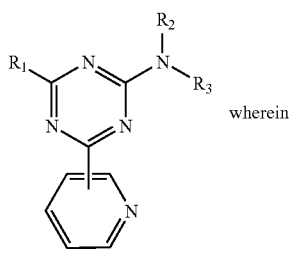

(1)

wherein $R_1$ is $C_1$–$C_{20}$alkyl; $C_3$–$C_7$cycloalkyl; or $C_1$–$C_{20}$perfluoroalkyl;

$R_2$ is hydrogen; $C_1$–$C_{20}$alkyl; or $C_3$–$C_7$cycloalkyl; and $R_3$ is hydrogen; $C_1$–$C_{20}$alkyl; $C_3$–$C_7$cycloalkyl; $C_1$–$C_{20}$perfluoroalkyl; $C_1$–$C_{20}$alkyl-carbonyl; $C_3$–$C_7$cycloalkyl-carbonyl; $C_1$–$C_{20}$perfluoroalkyl-carbonyl; or phenylcarbonyl.

$C_1$–$C_{20}$Alkyl radicals are straight-chain or branched alkyl radicals such as, for example, methyl, ethyl, n-propyl, isopropyl, n-butyl, sec-butyl, tert-butyl, amyl, isoamyl or tert-amyl, hexyl, 2-ethylhexyl, heptyl, octyl, isooctyl, nonyl, decyl, undecyl, dodecyl, tetradecyl, pentadecyl, hexadecyl, heptadecyl, octadecyl or eicosyl.

$C_3$–$C_7$Cycloalkyl is, for example, cyclopropyl, cyclobutyl, cyclopentyl, cycloheptyl and, especially, cyclohexyl. Those radicals may be substituted, for example by one or more identical or different $C_1$–$C_4$alkyl radicals, especially by methyl, and/or by hydroxy. When cycloalkyl radicals are substituted by one or more substituents, they are preferably substituted by one, two or four, especially one or two, identical or different substituents.

The invention relates preferably to compounds of formula (1) wherein $R_1$ is $C_1$–$C_4$alkyl;

$R_2$ is hydrogen; and $R_3$ is $C_6$–$C_{20}$alkyl; $C_3$–$C_7$cycloalkyl; $C_1$–$C_{20}$perfluoroalkyl; $C_1$–$C_{20}$alkyl-carbonyl; $C_3$–$C_7$cyclo-alkyl-carbonyl; or $C_1$–$C_{20}$perfluoroalkyl-carbonyl.

Very special preference is given to compounds of formula (1) wherein $R_1$ is $C_1$–$C_4$alkyl;

$R_2$ is hydrogen; and $R_3$ is $C_2$–$C_6$alkyl; $C_1$–$C_{12}$perfluoroalkyl; $C_1$–$C_{12}$alkyl-carbonyl; or $C_1$–$C_{12}$perfluoroalkyl-carbonyl.

Very special preference is given to compounds according to the invention that correspond to formula

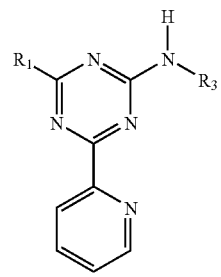

(2)

wherein $R_1$ is $C_1$–$C_4$alkyl; especially methyl; or tert-butyl; and $R_3$ is $C_6$–$C_{20}$alkyl; $C_2$–$C_6$alkyl; $C_3$–$C_7$cycloalkyl; $C_1$–$C_{20}$perfluoroalkyl; $C_1$–$C_{20}$alkyl-carbonyl; $C_3$–$C_7$cycloalkyl-carbonyl; or $C_1$–$C_{20}$perfluoroalkyl-carbonyl;

or to formula

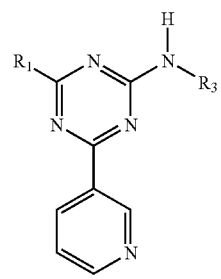

(3)

wherein $R_1$ is $C_1$–$C_4$alkyl; especially methyl; and $R_3$ is $C_6$–$C_{20}$alkyl; $C_3$–$C_7$cycloalkyl; $C_1$–$C_{20}$perfluoroalkyl; $C_1$–$C_{20}$alkyl-carbonyl; or $C_1$–$C_{20}$perfluoroalkyl-carbonyl;

or to formula

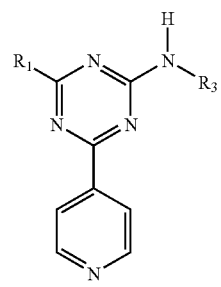

(4)

wherein $R_1$ is $C_1$–$C_4$alkyl; especially tert-butyl; and $R_3$ is $C_6$–$C_{20}$alkyl; $C_3$–$C_7$cycloalkyl; $C_1$–$C_{20}$perfluoroalkyl; $C_1$–$C_{20}$alkyl-carbonyl;$C_3$–$C_7$cyclo-alkyl-carbonyl; or $C_1$–$C_{20}$perfluoroalkyl-carbonyl.

Very special preference is given to compounds of formula (2) wherein $R_1$ is tert-butyl; and $R_3$ is $C_6$–$C_{20}$alkyl; especially octyl.

Preparation of the triazine derivatives according to the invention is carried out using processes known per se and, depending on the basic structure, may be carried out in accordance with one or more of the methods described hereinbelow.

Synthesis of the triazines of the general formula (1) wherein $R_1$=methyl is preferably carried out as follows: first, pyridylamidines known from the literature (for example, from Medwid, J. Med. Chem., 1990 (33). 1230), where appropriate in the form of their salts, are reacted with cyano-imidates, which have been prepared in accordance with data in the literature, for example as described in WO/0014056, or which are commercially available, preferably cyano-methyl-imidates of formula (1c), in an inert solvent, preferably methanol, to form the amino-methyl-triazines of formula (1d). The latter compounds are then, in accordance with processes known from the literature (for example, Beckwith, The Chemistry of Amides, Wiley, 1970 (86)), acylated with carboxylic acids or derivatives thereof, preferably with carboxylic anhydrides, to form the N-acyl-amino-triazines of formula (1e), which are subsequently reduced using reducing agents such as, for example, hydrogen, simple or complex metal hydrides, transition metals or salts thereof, but preferably using borane, to form the N-alkyl-amino-triazines of formula (1a).

The reaction sequence can be illustrated by the following Scheme:

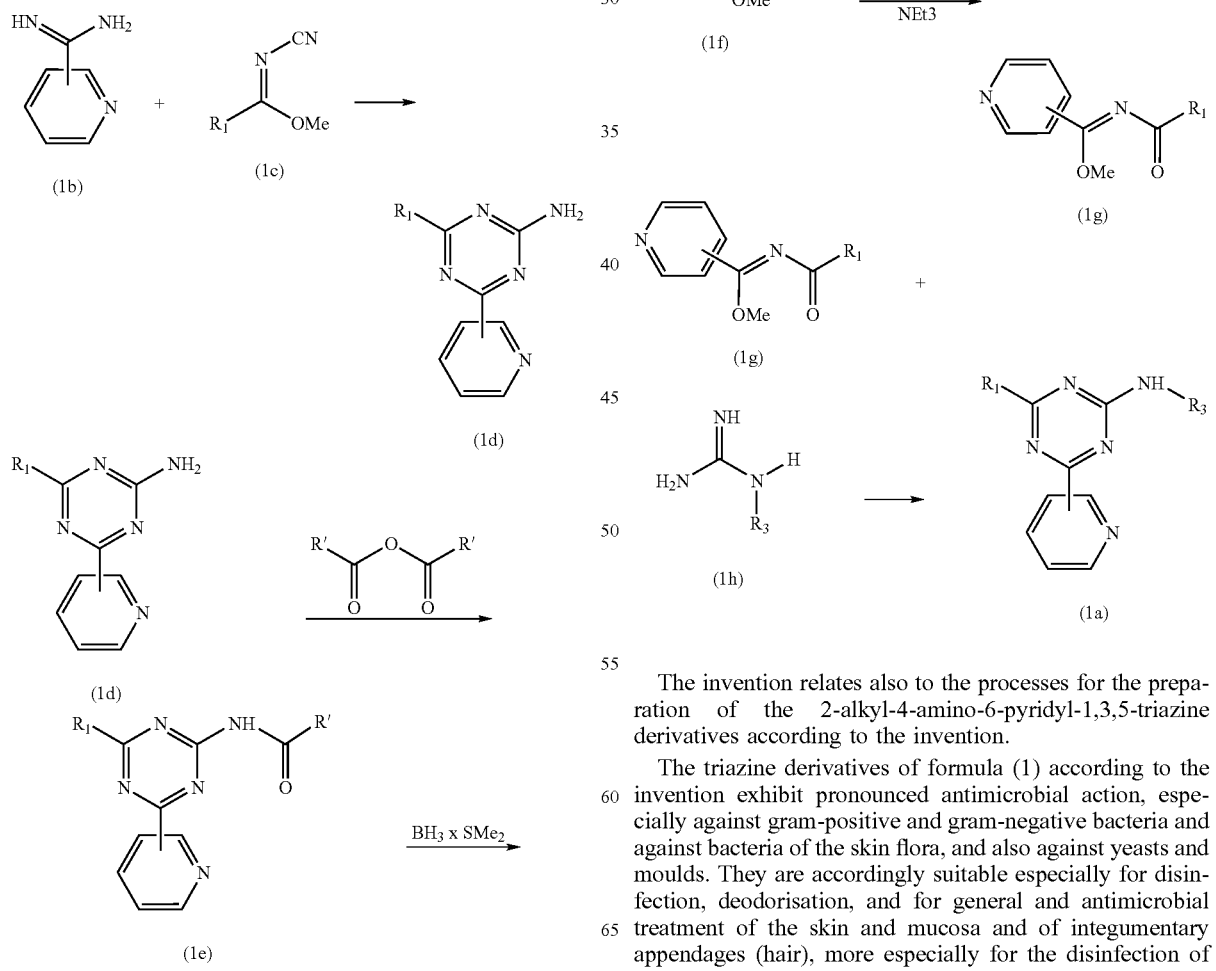

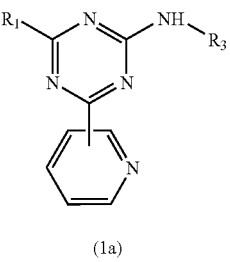

In another process, 2-alkyl-triazines can be prepared by condensation of N-acylated imino esters with substituted guanidines. For that purpose, pyridylimino esters of formula (1f), which have been prepared in accordance with data In the literature or which are commercially available, are acylated in accordance with customary methods, and the resulting N-acyl-imino esters of formula (1g) are reacted with mono- or di-substituted guanidines or salts thereof in an inert solvent, preferably isopropanol or tert-butanol, to form the pyridyl-triazines of formula (1a):

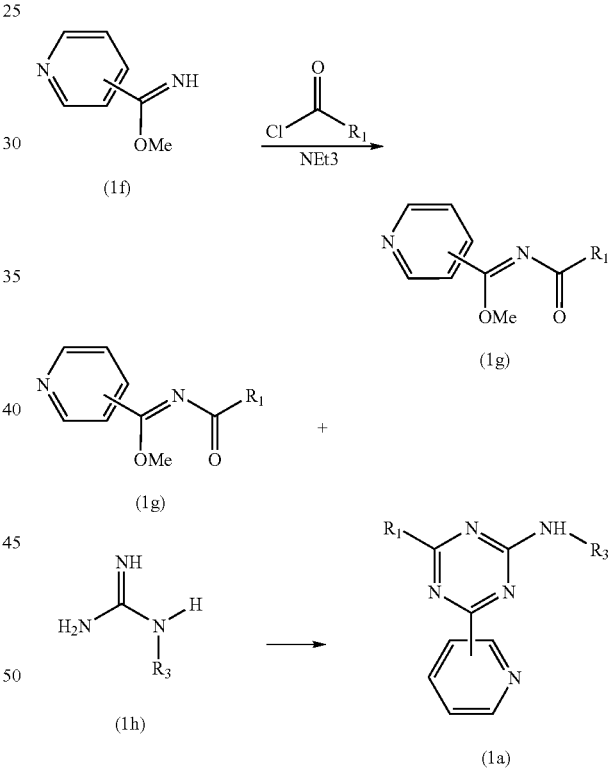

The invention relates also to the processes for the preparation of the 2-alkyl-4-amino-6-pyridyl-1,3,5-triazine derivatives according to the invention.

The triazine derivatives of formula (1) according to the invention exhibit pronounced antimicrobial action, especially against gram-positive and gram-negative bacteria and against bacteria of the skin flora, and also against yeasts and moulds. They are accordingly suitable especially for disinfection, deodorisation, and for general and antimicrobial treatment of the skin and mucosa and of integumentary appendages (hair), more especially for the disinfection of hands and wounds.

They are accordingly suitable as antimicrobial active substances and preservatives in personal care preparations such as, for example, shampoos, bath additives, haircare preparations, liquid and solid soaps (based on synthetic surfactants and salts of saturated and/or unsaturated fatty acids), lotions and creams, deodorants, other aqueous or alcoholic solutions, e.g. cleansing solutions for the skin, moist cleansing cloths, oils or powders.

The invention accordingly relates also to a personal care preparation comprising at least one compound of formula (1) and cosmetically tolerable carriers or adjuvants.

The personal care preparation according to the invention contains from 0.01 to 15% by weight, preferably from 0.1 to 10% by weight, based on the total weight of the composition, of a compound of formula (1), and cosmetically tolerable adjuvants.

Depending upon the form of the personal care preparation, it comprises, in addition to the triazine derivative of formula (1), further constituents such as, for example, sequestering agents, colorants, perfume oils, thickeners or solidifiers (consistency regulators), emollients, UV-absorbers, skin protective agents, antioxidants, additives that improve the mechanical properties, such as dicarboxylic acids and/or aluminium, zinc, calcium or magnesium salts of $C_{14}$–$C_{22}$ fatty acids, and, optionally, preservatives.

The personal care preparation according to the invention may be formulated as a water-in-oil or oil-in-water emulsion, an alcoholic or alcohol-containing formulation, a vesicular dispersion of an ionic or non-ionic amphiphilic lipid, a gel, a solid stick or an aerosol formulation.

As a water-in-oil or oil-in-water emulsion, the cosmetically tolerable adjuvant contains preferably from 5 to 50% of an oil phase, from 5 to 20% of an emulsifier and from 30 to 90% water. The oil phase may comprise any oil suitable for cosmetic formulations such as, for example, one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Cosmetic formulations according to the invention are used in various fields. There come into consideration, for example, especially the following preparations:

skin-care preparations, e.g. skin-washing and cleansing preparations in the form of tablet-form or liquid soaps, synthetic detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascaras, eyeliners, eye creams or eye-fix creams; lip-care preparations, e.g. lipsticks, lip gloss, lip contour pencils, nail-care preparations, such as nail varnish, nail varnish removers, nail hardeners or cuticle removers;

intimate hygiene preparations, e.g. intimate washing lotions or intimate sprays;

foot-care preparations, e.g. foot baths, foot powders, foot creams or foot balsams, special deodorants and antiperspirants or callus-removing preparations;

light-protective preparations, such as sun milks, lotions, creams or oils, sun-blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

dental care, denture-care and mouth-care preparations, e.g. toothpastes, gel toothpastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidising dyes, or natural hair colorants, such as henna or camomile.

An antimicrobial soap has, for example, the following composition:

0.01 to 5% by weight of a compound of formula (1)
0.3 to 1% by weight titanium dioxide,
1 to 10% by weight stearic acid,
soap base ad 100%, e.g. a sodium salt of tallow fatty acid or coconut fatty acid, or glycerol.

A shampoo has, for example, the following composition:
0.01 to 5% by weight of a compound of formula (1),
12.0% by weight sodium laureth-2-sulfate,
4.0% by weight cocamidopropyl betaine,
3.0% by weight NaCl and
water ad 100%.

A deodorant has, for example, the following composition:
0.01 to 5% by weight of a compound of formula (1),
60% by weight ethanol,
0.3% by weight perfume oil, and
water ad 100%.

The invention relates also to an oral composition containing from 0.01 to 15% by weight, based on the total weight of the composition, of a compound of formula (1), and orally tolerable adjuvants.

Example of an Oral Composition:
10% by weight sorbitol,
10% by weight glycerol,
15% by weight ethanol,
15% by weight propylene glycol,
0.5% by weight sodium lauryl sulfate,
0.25% by weight sodium methylcocyl taurate,
0.25% by weight polyoxypropylene/polyoxyethylene block copolymer,
0.10% by weight peppermint flavouring,
0.1 to 0.5% by weight of a compound of formula (1), and
48.6% by weight water.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

The triazine derivatives of formula (1) according to the Invention are also suitable for treating, especially preserving, textile fibre materials. Such materials are undyed and dyed or printed fibre materials, for example of silk, wool, polyamide or polyurethanes, and especially cellulosic fibre materials of all kinds. Such fibre materials are, for example, natural cellulose fibres, such as cotton, linen, jute and hemp, as well as cellulose and regenerated cellulose. Preferred suitable textile fibre materials are made of cotton.

The triazine derivatives of formula (1) according to the invention are suitable also for treating plastics, especially imparting antimicrobial properties to or preserving plastics, such as, for example, polyethylene, polypropylene, polyurethane, polyester, polyamide, polycarbonate, latex etc. Fields of use therefor are, for example, floor coverings, plastics coatings, plastics containers and packaging materials; kitchen and bathroom utensils (e.g. brushes, shower curtains, sponges, bathmats), latex, filter materials (air and water filters), plastics articles used in the field of medicine such as, for example, dressing materials, syringes, catheters etc., so-called "medical devices", gloves and mattresses.

Paper, for example papers used for hygiene purposes, may also be provided with antimicrobial properties using the triazine derivatives of formula (1) according to the invention.

It is also possible for nonwovens such as, for example, nappies/diapers, sanitary towels, panty liners, and cloths for hygiene and household uses, to be provided with antimicrobial properties in accordance with the invention.

The triazine derivatives of formula (1) are also used in washing and cleaning formulations such as, for example, liquid or powder washing agents or softeners.

The triazine derivatives of formula (1) can also be used especially in household and general-purpose cleaners for cleaning and disinfecting hard surfaces.

A cleaning preparation has, for example, the following composition:

| | |
|---|---|
| 0.01 to 5% | of a compound of formula (1) |
| 3.0% | octyl alcohol 4EO |
| 1.3% | fatty alcohol $C_8$–$C_{10}$ polyglucoside |

-continued

| | |
|---|---|
| 3.0% | isopropanol |
| water | ad 100%. |

In addition to preserving cosmetic and household products, the preservation of technical products, the provision of technical products with antimicrobial properties and use as a biocide in technical processes are also possible, for example in paper treatment, especially in paper treatment liquors, printing thickeners of starch or cellulose derivatives, surface-coatings and paints.

The triazine derivatives of formula (1) according to the invention are also suitable for the antimicrobial treatment of wood and for the antimicrobial treatment of leather, the preserving of leather and the provision of leather with antimicrobial properties.

The triazine derivatives of formula (1) according to the invention are also suitable for the protection of cosmetic products and household products from microbial damage.

In addition to their generally antimicrobial action, the triazine derivatives of formula (1) according to the invention are moreover capable of penetrating biofilms on living and non-living surfaces, of preventing the adhesion of bacteria to surfaces and any further build-up of the biofilm, of detaching such build-up, and/or of inhibiting the further growth of the biofilm-forming micro-organisms in the biological matrix or of killing such micro-organisms.

Biofilms are understood, very generally, to be aggregations of living and dead micro-organisms, especially bacteria, that adhere to living and non-living surfaces, In conjunction with their metabolites in the form of extracellular polymeric substances (EPS matrix), e.g. polysaccharides. The activity of antimicrobial substances that normally exhibit a pronounced growth-inhibiting or lethal action with respect to planktonic cells may be greatly reduced with respect to micro-organisms that are organised in biofilms, for example because of inadequate active substance penetration into the biological matrix.

In the present invention, this relates, very especially, to biofilms on human tooth surfaces and oral mucosa, which play a crucial role in the onset of degenerative diseases in the oral cavity, e.g. caries or periodontitis, as a result of the micro-organisms that are formed or their metabolites.

The following Examples illustrate, but do not limit, the present invention.

EXAMPLE 1

Synthesis of
2-amino-4-methyl-6-pyrid-2-yl-1,3,5-triazine

Reaction Scheme:

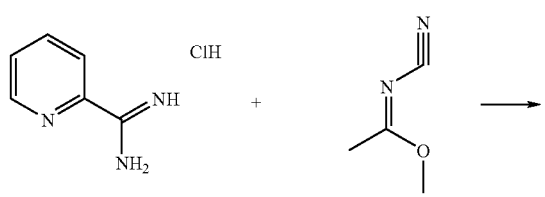

-continued

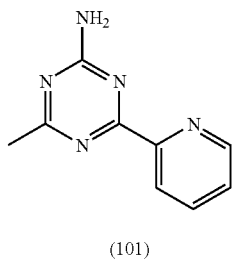

(101)

A solution of 17.0 g (0.32 mol) of sodium methoxide in 60 ml of methanol is added dropwise, at room temperature, to a solution of 50.0 g (0.32 mol) of pyrid-2-ylamidine hydrochloride in 240 ml of methanol. After stirring for 20 minutes, filtration is carried out and the solution is then added dropwise to 31.4 g (0.32 mol) of methyl-N-cyanoethanimidate, with stirring. After stirring for 2 hours at room temperature, cooling to 0° C. is carried out and the precipitate is subsequently filtered off.

The compound of formula (101) is purified by re-crystallisation from ethanol.

Yield: 30.0 g (50% of theory)

$^1$H NMR (CDCl$_3$): 7.35–8.75 (m,4H,arom. H), 6.00 (s,2H,NH$_2$), 2.50 (s,3H,CH$_3$)

$^{13}$C NMR (CDCl$_3$): 177.8/171.0/167.7 (triazine C's), 153.9/150.4/137.7/126.4/124.6 (pyridine C's), 26.0 (CH$_3$)

m/z=187 (GC/MS)

Synthesis of the homologous 3-pyridyl derivative of formula

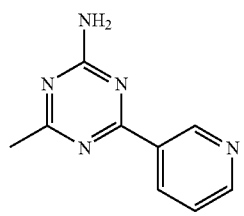

(102)

is carried out analogously.

$^1$H NMR (DMSO-d$_6$): 8.20–9.50 (m,4H,arom. H), 8.15 (s,2H,NH$_2$), 2.45 (s,3H,CH$_3$)

$^{13}$C NMR (DMSO-d$_6$): 174.8/166.0/165.2 (triazine C's), 145.3/144.1/142.3/133.8/127.6 (pyridine C's), 24.5 (CH$_3$)

m/z=187 (GC/MS)

EXAMPLE 2

Preparation of 2-acetylamino-4-methyl-6-pyrid-2-yl-1,3,5-triazine

Reaction Scheme

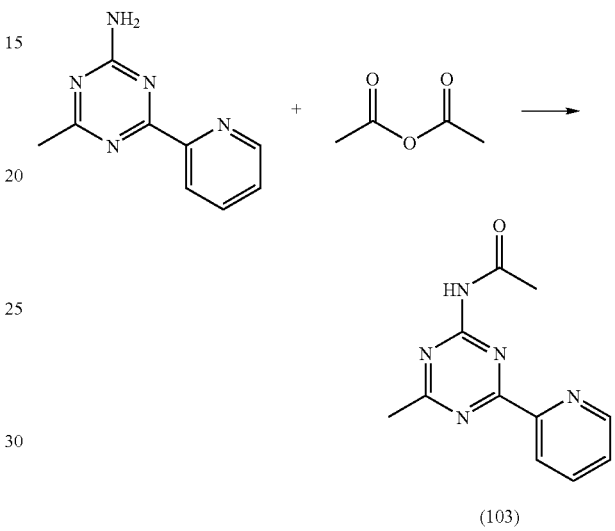

1.9 g (10 mmol) of formula (102) from Example 1 are stirred in 5 ml of acetanhydride for 12 hours at 100° C. After concentration, the residue is taken up in methylene chloride and washed with NaHCO$_3$ solution. The compound of formula (103) is obtained quantitatively and in a purity that is sufficient for the subsequent reaction (>95% GC).

$^1$H NMR (CDCl$_3$): 7.41–8.81 (m,4H, arom. H), 8.42 (s,1H,NH), 2.68 (s,3H,CH$_3$), 2.58 (s,3H,CH$_3$)

$^{13}$C NMR (CDCl$_3$): 179.4/171.61171.4/164.1 (triazine C's/CO), 153.0/150.7/137.7/127.0/125.0 (pyridine C's), 26.5 (CH$_3$), 26.2 (CH$_3$)

The following N-acylamino-triazines are obtained analogously (Table 1):

TABLE 1

| Compound of formula | Structure | Method of analysis | Purity [% (FID)] |
|---|---|---|---|
| (104) | <br>F F F F F<br>structure with triazine-NH-C(O)-C$_4$F$_9$ and 2-pyridyl | GC-MS | 47 |

TABLE 1-continued

| Compound of formula | Structure | Method of analysis | Purity [% (FID)] |
|---|---|---|---|
| (105) | 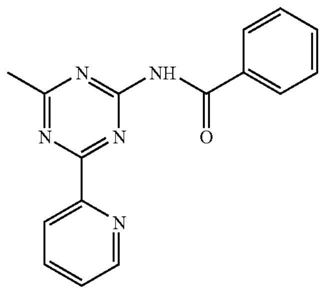 | GC-MS | 73 |
| (106) | 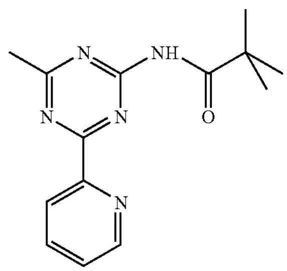 | GC-MS | 70 |
| (107) | 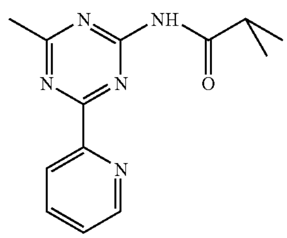 | GC-MS | 82 |
| (108) | 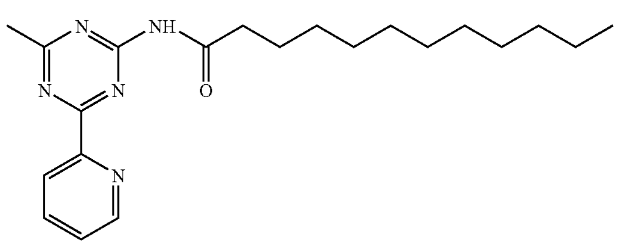 | GC-MS | 58 |
| (109) | 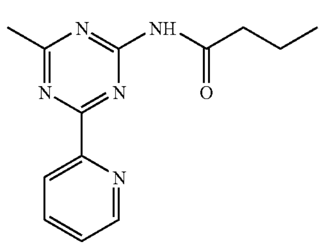 | GC-MS | 81 |
| (110) | 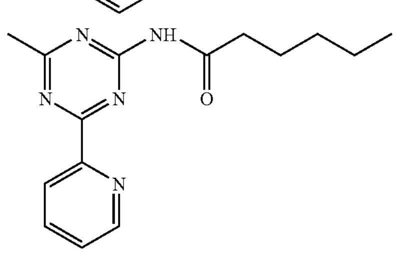 | GC-MS | 70 |

TABLE 1-continued

| Compound of formula | Structure | Method of analysis | Purity [% (FID)] |
|---|---|---|---|
| (111) | 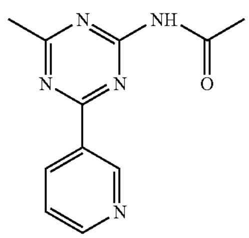 | GC-MS | 80 |
| (112) | 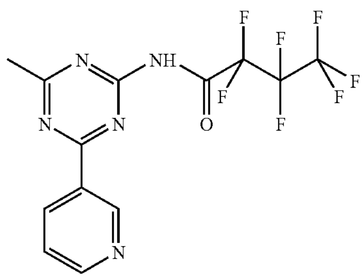 | GC-MS/LC-MS | 30 |
| (113) | 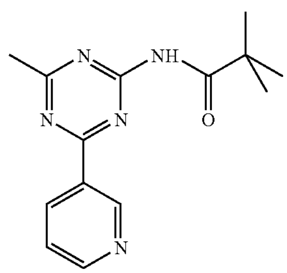 | GC-MS | 89 |
| (114) | 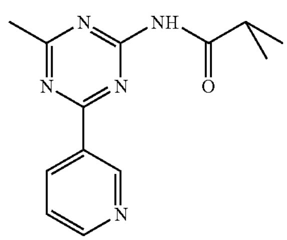 | GC-MS | 92 |
| (115) | 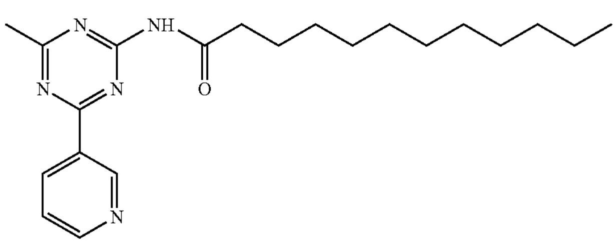 | GC-MS | 20 |
| (116) | 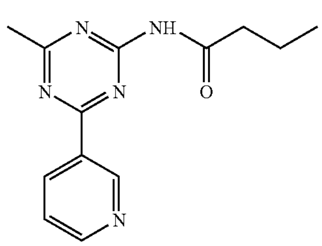 | GC-MS | 59 |

TABLE 1-continued

| Compound of formula | Structure | Method of analysis | Purity [% (FID)] |
|---|---|---|---|
| (117) | 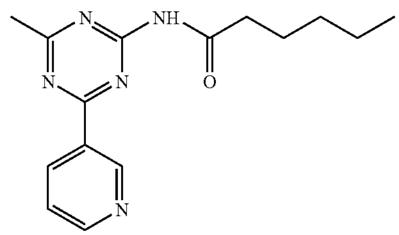 | GC-MS | 70 |
| (118) | 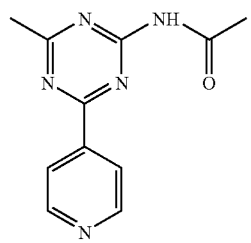 | GC-MS | 90 |
| (119) | 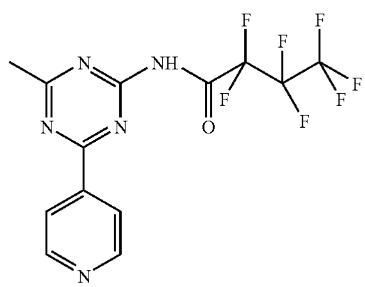 | GC-MS | 72 |
| (120) | 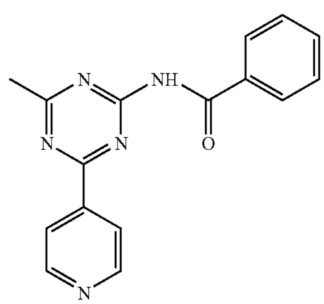 | GC-MS | 87 |
| (121) | 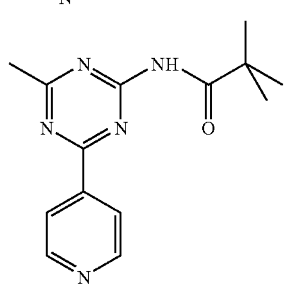 | GC-MS | 97 |
| (122) | 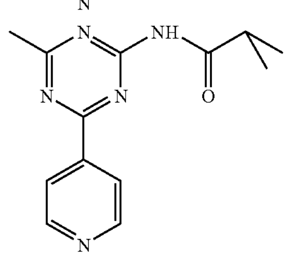 | GC-MS | 79 |

TABLE 1-continued

| Compound of formula | Structure | Method of analysis | Purity [% (FID)] |
|---|---|---|---|
| (123) | 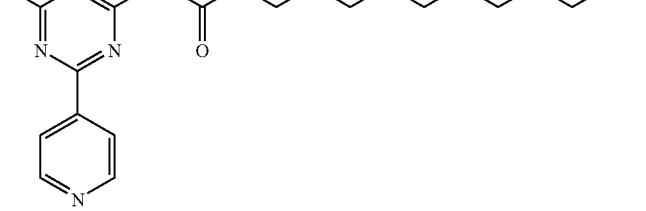 | GC-MS | 42 |
| (124) | 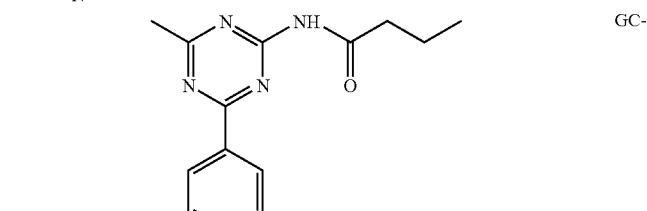 | GC-MS | 90 |
| (125) | 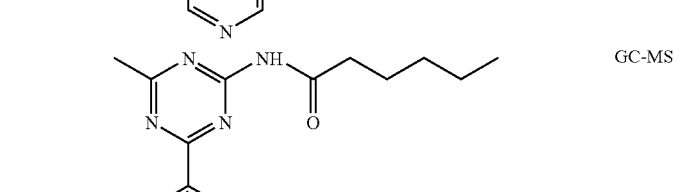 | GC-MS | 86 |
| (126) | 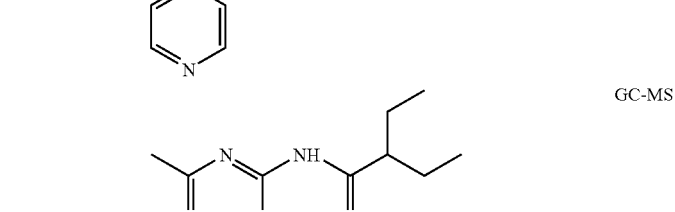 | GC-MS | 35 |

EXAMPLE 3

General Synthesis of 2-alkylamino-4-methyl-6-pyridyl-1,3,5-triazines

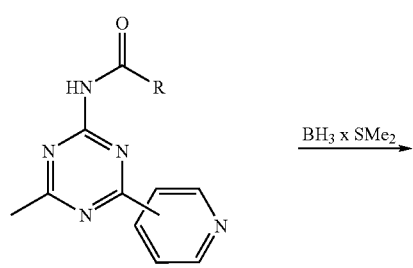

$\xrightarrow{BH_3 \times SMe_2}$

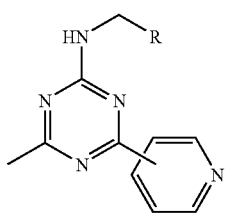

To 1 mmol of the acylamino-triazine in 1 ml of toluene there is added, at 0° C., the stoichiometric amount of a 2M solution of borane-dimethyl sulfide complex in toluene, and heating at reflux is then carried out for 4 hours. After cooling to room temperature, the reaction solution is treated with 10% Na$_2$CO$_3$ solution, dried and concentrated by evaporation. The identity of the reaction products is confirmed by GC/MS or LC/MS and the compounds are used for screening against micro-organisms without further purification. The following compounds are obtained in that manner:

TABLE 2

| Compound of formula | Structure | Method of analysis | Purity [% (FID)] |
| --- | --- | --- | --- |
| (127) | 4-methyl-6-(pyridin-2-yl)-N-ethyl-1,3,5-triazin-2-amine | GC-MS | 69 |
| (128) | 4-methyl-6-(pyridin-2-yl)-N-neopentyl-1,3,5-triazin-2-amine | GC-MS | 30 |
| (129) | 4-methyl-6-(pyridin-2-yl)-N-isobutyl-1,3,5-triazin-2-amine | GC-MS | 66 |
| (130) | 4-methyl-6-(pyridin-2-yl)-N-butyl-1,3,5-triazin-2-amine | GC-MS | 90 |
| (131) | 4-methyl-6-(pyridin-2-yl)-N-hexyl-1,3,5-triazin-2-amine | GC-MS | 60 |
| (132) | 4-methyl-6-(pyridin-3-yl)-N-ethyl-1,3,5-triazin-2-amine | GC-MS | 100 |

TABLE 2-continued

| Compound of formula | Structure | Method of analysis | Purity [% (FID)] |
|---|---|---|---|
| (133) | 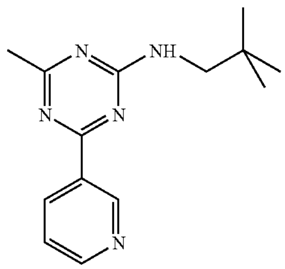 | GC-MS | 100 |
| (134) | 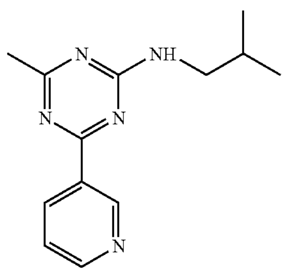 | GC-MS | 100 |
| (135) | 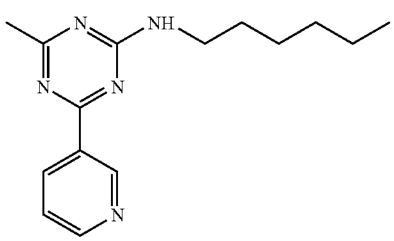 | GC-MS | 40 |
| (136) | 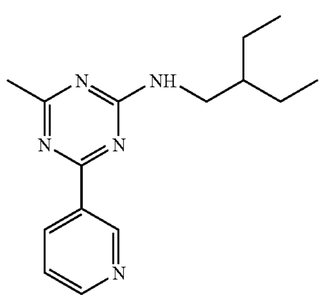 | GC-MS | 30 |
| (137) | 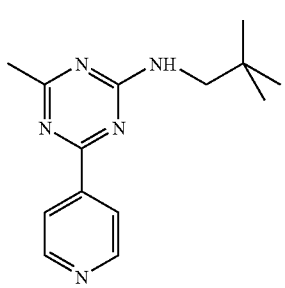 | GC-MS | 92 |

TABLE 2-continued

| Compound of formula | Structure | Method of analysis | Purity [% (FID)] |
|---|---|---|---|
| (138) | ![structure] | GC-MS | 35 |
| (139) | ![structure] | GC-MS | 57 |

EXAMPLE 4

Synthesis of 2-tert-butyl-4-n-octylamino-6-pyrid-2-yl-1,3,5-triazine (Compound of Formula (140))

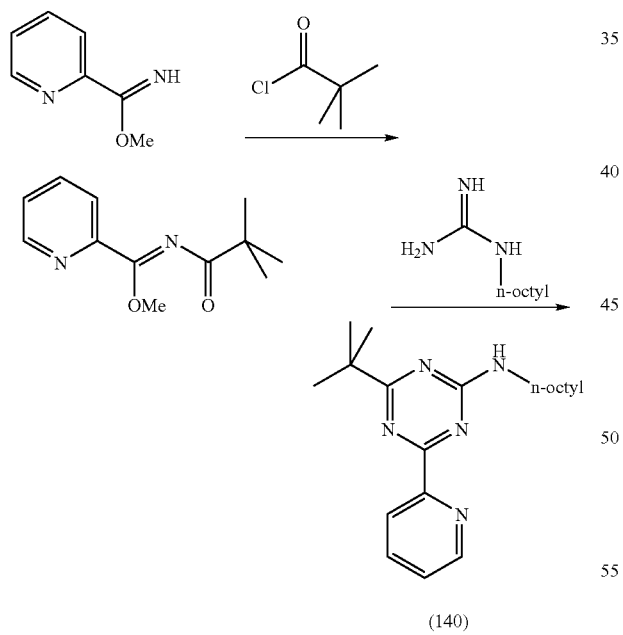

(140)

2.60 g (21.5 mmol) of pivaloyl chloride in 10 ml of toluene are slowly added to 2.66 g (19.5 mmol) of 2-pyridylimidomethyl ester and 2.17 g (21.5 mmol) of NEt$_3$ in 30 ml of toluene at 0° C. After stirring for 24 hours at room temperature, filtration is carried out and the solvent is drawn off. The residue is taken up in 10 ml of tert-butanol, and a solution of 6.61 g (30 mmol) of n-octylguanidine in 20 ml tert-butanol is then added.

After 24 hours at room temperature, the solvent is drawn off and the compound of formula (140) is purified by chromatography on silica gel (ethyl acetate/hexane 9/1).

Yield: 5.1 g (77% of theory)

$^1$H NMR (CDCl$_3$): 7.33–8.73 (m,4H,arom. H), 5.79 (s,1H,NH), 1.54 (m,2H,CH$_2$), 1.20–1.33 (m,21H, CH$_2$/C(CH$_3$)$_3$), 0.81 (t,3H,CH$_3$)

$^{13}$C NMR (CDCl$_3$): 186.3/169.7/166.8 (triazine C's), 154.7/150.2/137.3/125.9/124.7 (pyridyl C's), 39.7/29.2 (C(CH$_3$)$_3$), 14.5 (CH$_3$), 23.0–41.3 (CH$_2$)

m/z=341

EXAMPLE 5

Determination of the Minimum Inhibitory Concentration (MIC) in the Agar Incorporation Test (MIC Test)

| | |
|---|---|
| Medium: | Casein/soymeal peptone agar (Merck) |
| | *Sabouraud 4% glucose agar (Merck) |
| Diluent: | Sterile 0.85% NaCl solution |
| Test organisms: | *Staphylococcus aureus* ATCC 6538 |
| | *Staphylococcus epidermidis* ATCC 12228 |
| | *Corynebacterium xerosis* ATCC 373 |
| | *C. minutissimum* ATCC 23348 |
| | *Propionibacterium acnes* ATCC 6919 |
| | *Escherichia coli* ATCC 10536 |
| | *Escherichia coli* NCTC 8196 |
| | *Proteus vulgaris* ATCC 6896 |
| | *Klebsiella pneumoniae* ATCC 4352 |
| | *Salmonella choleraesuis* ATCC 9184 |
| | *Pseudomonas aeruginosa* ATCC 15442 |
| | *Candida albicans* ATCC 10231 |
| | *Aspergillus niger* ATCC 6275 |
| Incubation: | 24 hours at 37° C. |
| | *3 days at 28° C. |
| Test solution: | 1% stock solutions of all the test substances are prepared in a suitable solvent and diluted in serial dilutions to end concentrations of from 1000 ppm to 10 ppm. |

-continued

| Test principle: | 0.3 ml of each dilution step is mixed with 15 ml of nutrient medium while the latter is still liquid. After the nutrient medium has solidified, 10 µl of a suitable organism dilution of each of the test strains in 0.85% NaCl solution are spotted onto the agar medium: |
|---|---|
| Staphylococcus aureus ATCC 6538 | 1:100 |
| Staphylococcus epidermidis ATCC 12228 | 1:1000 |
| Corynebacterium xerosis ATCC 373 | 1:1000 |
| C. minutissimum ATCC 23348 | 1:10 dilution |
| Propionibacterium acnes ATCC 6919 | 1:10 dilution |

The plates are incubated at 37° C. for 24 hours (*A. niger* at 28° C. for 3 days) and then the highest dilution (lowest concentration) of the test substance at which growth is just no longer discernible (corresponds to the MIC) is determined.

The results are shown in Tables 3 and 4.

TABLE 3

MIC in [ppm]

| | Compound of formula (140) |
|---|---|
| Staphylococcus aureus ATCC 6538 | 0.94 |
| Staphylococcus epidermidis ATCC 12228 | 120 |
| Corynebacterium xerosis ATCC 373 | 0.94 |
| C. minutissimum ATCC 23348 | 0.94 |
| Propionibacterium acnes ATCC 6919 | 0.94 |
| Escherichia coli ATCC 10536 | 60 |
| Escherichia coli NCTC 8196 | 60 |
| Proteus vulgaris ATCC 6896 | >120 |
| Klebsiella pneumoniae ATCC 4352 | 120 |
| Salmonella choleraesuis ATCC 9184 | 120 |
| Pseudomonas aeruginosa ATCC 15442 | >120 |
| Candida albicans ATCC 10231 | >120 |
| Aspergillus niger ATCC 6275 | >120 |

TABLE 4

MIC in [ppm]

| Compound of formula | Staphylococcus aureus ATCC 6538 |
|---|---|
| (123) | 8 |
| (131) | 30 |
| (135) | 60 |

EXAMPLE 6

Testing the Substantivity of 2-tert-butyl-4-n-octylamino-6-pyrid-2-yl-1,3,5-triazine (140) on Hydroxyapatite and Determination of the Growth-Inhibiting Action Principle:

Hydroxyapatite discs (diameter 10 mm) are placed in artificial saliva (Deutsche Zahnärztliche Zeitschrift DZZ 5/2002) for 4 hours, rinsed 4 times in NaCl solution and then incubated for 30 minutes in an ethanolic solution of the test substance (140) at 5 ppm. The discs are then transferred to a Nunclon-surface titre plate (12 wells) and incubated at 37° C. for 24 hours in CASO nutrient medium inoculated with *Actinomyces viscosus* ATCC 43146 (about $10^5$/ml).

Result:

FIG. 1 shows the inhibition of the growth of *Actinomyces viscosus* by the test substance (140) following adsorption of the substance onto hydroxyapatite discs pre-treated with artificial saliva, compared to an untreated control. The substantivity is dependent upon presence of the saliva.

EXAMPLE 7

Testing the Activity of 2-tert-butyl-4-n-octylamino-6-pyrid-2-yl-1,3,5-triazine (140) in the Biofilm Model Principle: See Guggenheim et al. (2001), "Validation of an in vitro biofilm model of supragingival plaque", J. Dent Res. 80 (1).

Hydroxyapatite discs are pre-treated with human saliva and a biofilm of a defined mixed culture of various gram+ and gram− oral micro-organisms (Streptococci, *Actinomyces* sp., *Veillonella* & *Fusobacterium* sp. and others) and a yeast (*Candida albicans*) is allowed to grow on the hydroxyapatite. Over the course of the test, which lasts a total of 4 days, the discs are immersed several times in an application formulation of the substance (0.5% (140)). Finally, the biofilm is harvested and the living cell count is determined.

Result:

The results are shown in Table 3. The triazine compound causes a clear reduction in the microbial count of the biofilm on the hydroxyapatite discs, compared to the placebo formulation without active substance and a control containing 10% ethanol. A comparison substance, which exhibits no corresponding action, was also tested.

TABLE 3

| Sample | Control (10% ethanol) | Comparison substance | Compound of formula (140) | Placebo formulation |
|---|---|---|---|---|
| (Mean) [CPU/disc] | $4.9 \times 10^8$ | $1.6 \times 10^7$ | $1.1 \times 10^5$ | $1.4 \times 10^7$ |

Figure 1:
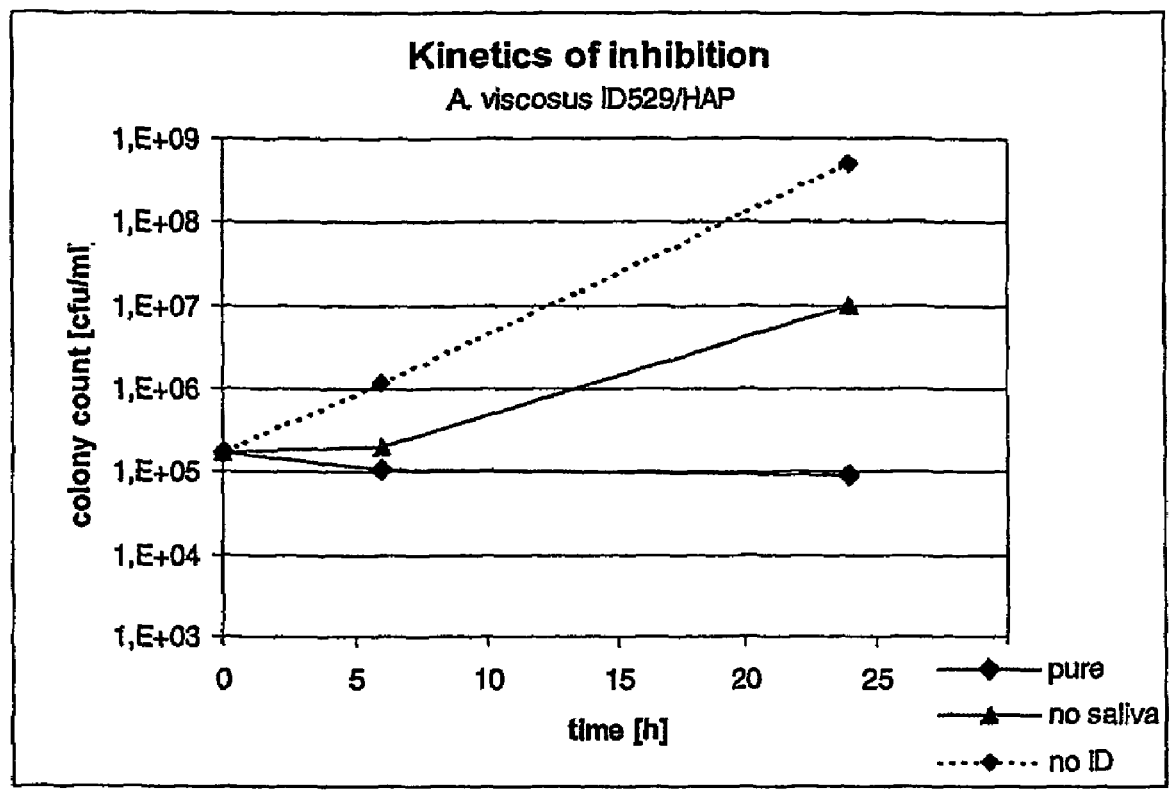
FIG. 1 shows the inhibition of the growth of *Actinomyces viscosus* by the test substance (140) following adsorption of the substance onto hydroxyapatite discs pre-treated with artificial saliva, compared to an untreated control.

What is claimed is:

1. A compound of formula (2)

wherein
$R_1$ is $C_1$–$C_4$alkyl; and
$R_3$ is $C_6$–$C_{20}$alkyl; $C_3$–$C_7$cycloalkyl; $C_1$–$C_{20}$perfluoroalkyl; $C_1$–$C_{20}$alkyl-carbonyl; $C_3$–$C_7$cycloalkyl-carbonyl; or $C_1$–$C_{20}$perfluoroalkyl-carbonyl.

2. A compound according to claim 1, wherein
$R_1$ is tert-butyl; and
$R_3$ is $C_6$–$C_{20}$alkyl.

3. A compound of formula

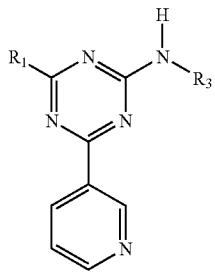

(3)

wherein
$R_1$ is $C_1$–$C_4$alkyl; and
$R_3$ is $C_6$–$C_{20}$alkyl; $C_3$–$C_7$cycloalkyl; $C_1$–$C_{20}$perfluoroalkyl; $C_1$–$C_{20}$alkyl-carbonyl; $C_3$–$C_7$cycloalkyl-carbonyl; or $C_1$–$C_{20}$perfluoroalkyl-carbonyl.

4. A compound of formula

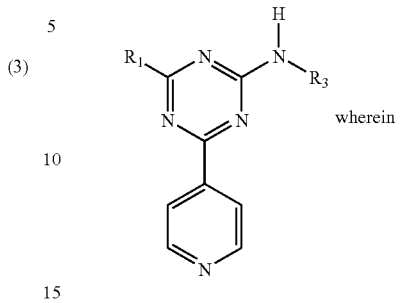

(4)

wherein $R_1$ is $C_1$–$C_4$alkyl; and
$R_3$ is $C_6$–$C_{20}$alkyl; $C_3$–$C_7$cycloalkyl; $C_1$–$C_{20}$perfluoroalkyl; $C_1$-$C_{20}$alkyl-carbonyl; $C_3$–$C_7$cycloalkyl-carbonyl; or $C_1$–$C_{20}$perfluoroalkyl-carbonyl.

* * * * *